(12) United States Patent
Moschel

(10) Patent No.: US 9,421,077 B2
(45) Date of Patent: *Aug. 23, 2016

(54) IMPLANTABLE SUPPORT WITH DILATOR ATTACHED TO ARM

(71) Applicant: Coloplast A/S, Humblebaek (DK)

(72) Inventor: Mark A. Moschel, Plymouth, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/574,404

(22) Filed: Dec. 18, 2014

(65) Prior Publication Data

US 2015/0105612 A1    Apr. 16, 2015

Related U.S. Application Data

(63) Continuation of application No. 14/149,952, filed on Jan. 8, 2014, now Pat. No. 8,944,992, which is a continuation of application No. 13/759,059, filed on Feb. 5, 2013, now Pat. No. 8,777,838.

(60) Provisional application No. 61/597,175, filed on Feb. 10, 2012.

(30) Foreign Application Priority Data

Feb. 9, 2012    (DK) .................................. 2012 70066

(51) Int. Cl.
| | |
|---|---|
| *A61F 2/00* | (2006.01) |
| *A61B 17/04* | (2006.01) |
| *A61B 17/00* | (2006.01) |
| *A61B 17/06* | (2006.01) |
| *A61B 17/42* | (2006.01) |

(52) U.S. Cl.
CPC ......... *A61F 2/0045* (2013.01); *A61B 17/0482* (2013.01); *A61F 2/0063* (2013.01); *A61B 17/42* (2013.01); *A61B 2017/00805* (2013.01); *A61B 2017/06052* (2013.01); *A61B 2017/06057* (2013.01); *A61F 2220/0008* (2013.01); *A61F 2230/0067* (2013.01)

(58) Field of Classification Search
CPC ...... A61F 2/00; A61F 2/0004; A61F 2/0031; A61F 2/0036; A61F 2/0045; A61F 2/0063; A61F 2/0077; A61B 17/0482
See application file for complete search history.

(56) References Cited

U.S. PATENT DOCUMENTS

2009/0171142 A1*    7/2009    Chu .................... A61B 17/0401
                                                                    600/37

* cited by examiner

*Primary Examiner* — Charles A Marmor, II
*Assistant Examiner* — Carrie R Dorna
(74) *Attorney, Agent, or Firm* — Coloplast Corp., Coloplast A/S; Nick Baumann

(57) ABSTRACT

A pelvic organ prolapse treatment device includes an implantable support sized to support and treat a prolapsed organ of a patient, a suture, a knot separate from the suture, and a dilator. The implantable support includes an arm having a first portion connected to a body of the implantable support and an end portion extending away from the body of the implantable support. The end portion of the arm is folded to include a first fold and a second fold that combine to reduce a lateral dimension of a portion of the end portion of the arm. The suture extends away from the end portion of the arm. The knot is provided separately from the suture and is secured around the first fold and the second fold to capture both the end portion of the arm and the suture. The dilator is disposed over and connected to the knot.

15 Claims, 9 Drawing Sheets

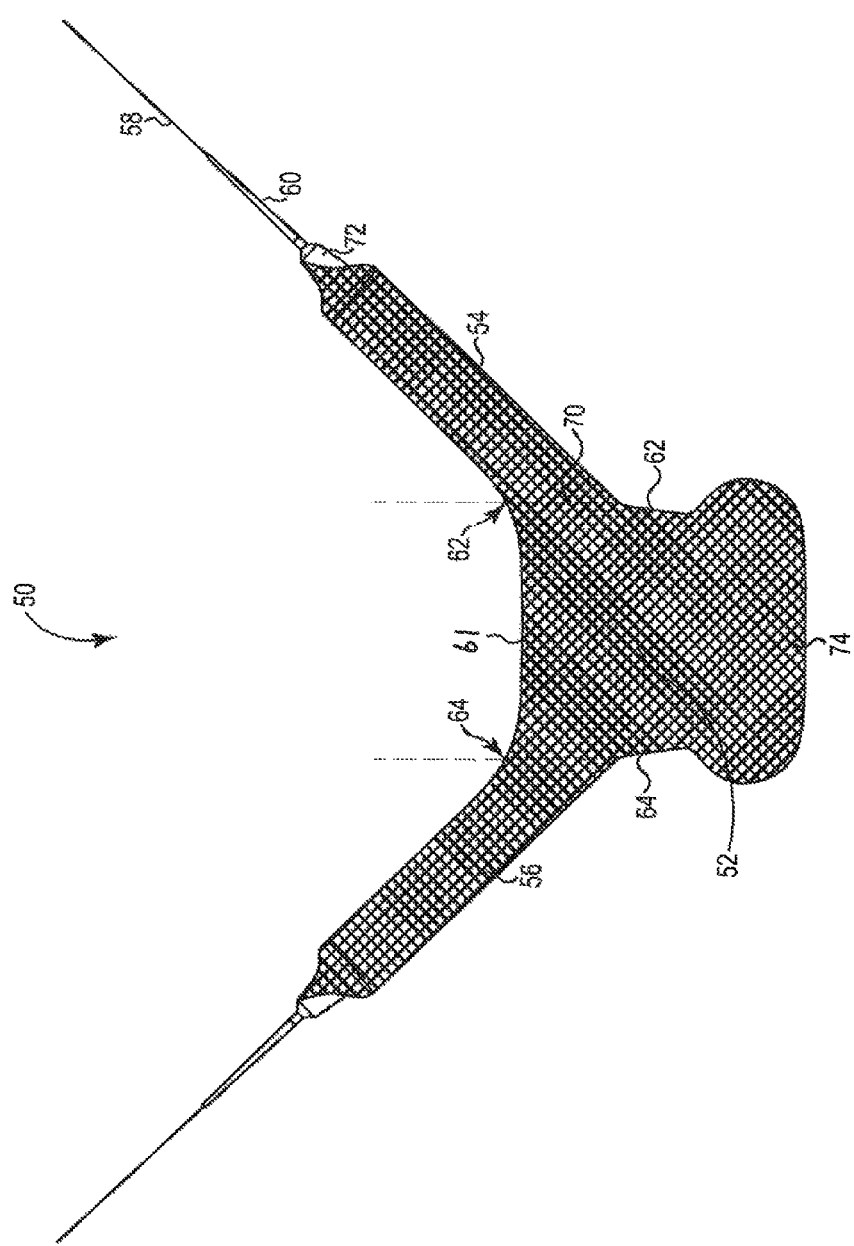

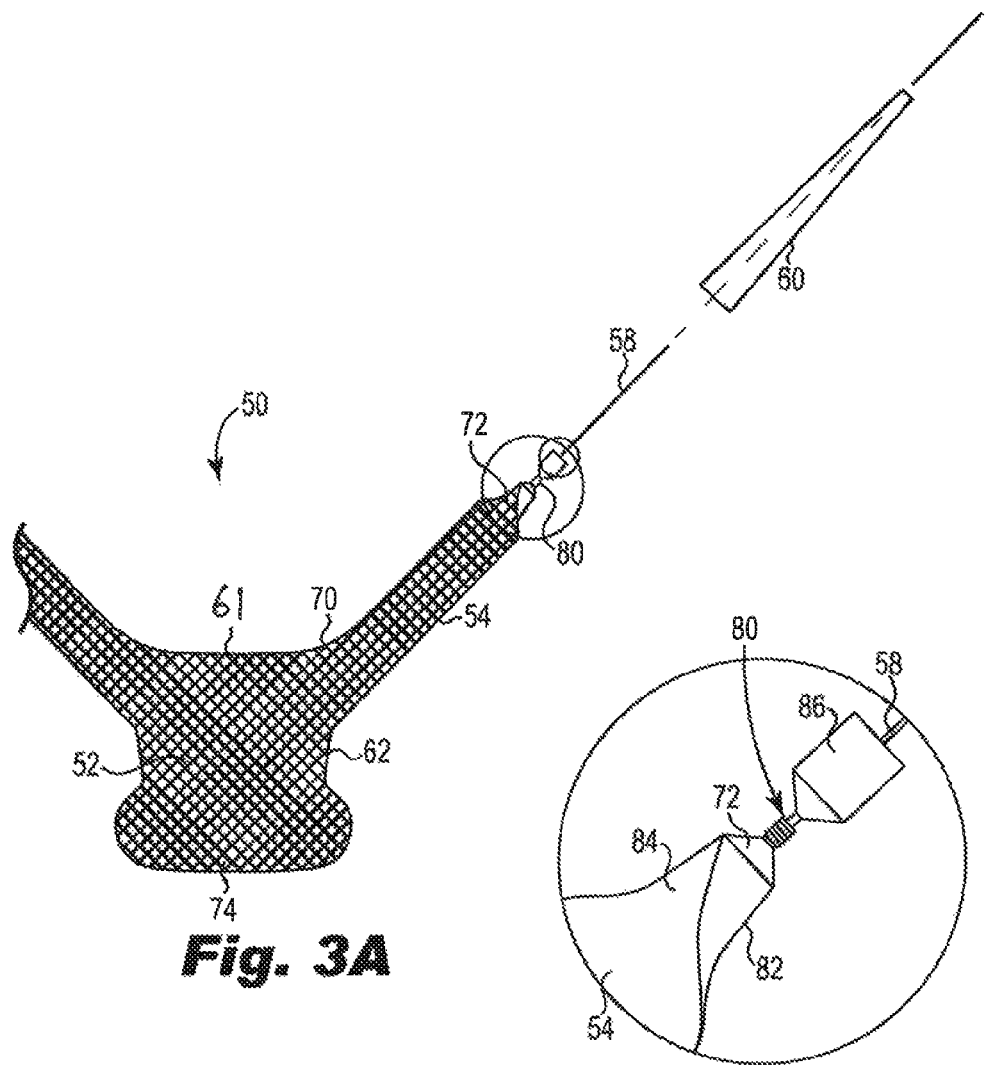
Fig. 3A
Fig. 3B
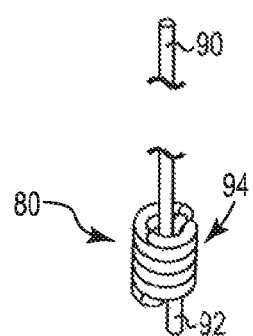
Fig. 3C

SECTION A-A

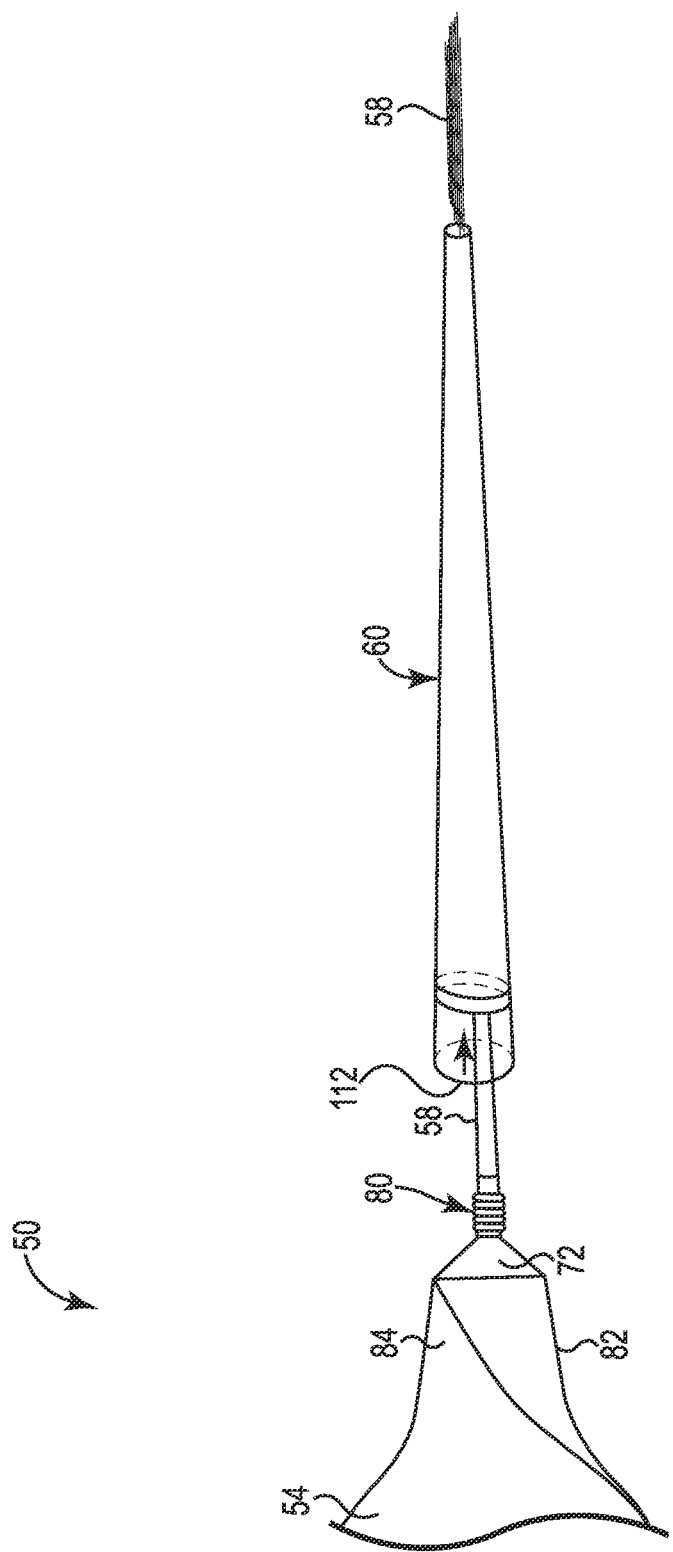

IMPLANTABLE SUPPORT WITH DILATOR ATTACHED TO ARM

BACKGROUND

Supports that are implanted to treat pelvic organ prolapse are generally secured to an anatomical structure within the pelvis. Typically the support is placed inside the pelvis by attaching a suture line to a tissue landmark, attaching the support to the suture line, and pulling on the suture line until the support is located at the landmark. Access to the pelvis is sometimes gained through an incision formed in the vagina. Placement and retrieval of the suture line through the tissue landmark can present challenges.

FIG. 1A is a schematic side view of a prior art suture line 10 attached to a support 12 by a joint 14. Suitable exemplary supports 12 include suture (shown) or support fabrics or arms attached to other implantable devices. Examples of the joint 14 includes a knot (shown) formed in the suture line 10 or other chemical or mechanical joints that attach the retrieval suture 10 to the support 12. The suture line 10 is directed through a tissue landmark 16 (for example a ligament) until the support 12 is placed in the location desired by the surgeon, after which the joint 14 and any excess portion of the support is trimmed off.

FIG. 1B is a schematic side view of the joint 14 pulled over the tissue landmark 16. Some joints 14 can undesirably drag, snag, or catch on the tissue landmark 16 and resist movement of the suture line 10 through the tissue landmark 16.

FIG. 1C is a schematic side view of the joint 14 undesirably hung up on and impeding movement of the support 12 into the tissue landmark 16. In some cases, the joint 14 tears the tissue landmark as the surgeon pulls on the suture line 10, which necessitates the placement of another suture line and support. In some cases, the surgeon prefers to place the suture line 10 at a different location and a snagged joint 14 will undesirably impede the surgeon's attempt to remove and relocate the suture line 10.

Surgeons and surgical staff would welcome improvements made to the placement of pelvic organ prolapse supports.

SUMMARY

One aspect provides a pelvic organ prolapse treatment device. The device includes an implantable support configured to treat a prolapsed area of a patient such as urethrocele prolapse, cystocele prolapse, vault prolapse, uterine prolapse, enterocele prolapse, or rectocele prolapse. The support includes a body portion and an arm connected to the body portion, a knot connecting a suture to an end portion of the arm, and a tubular dilator disposed over and permanently connected to the knot. The tubular dilator has an aspect ratio of greater than 7.

BRIEF DESCRIPTION OF THE DRAWINGS

The accompanying drawings are included to provide a further understanding of embodiments and are incorporated in and constitute a part of this specification.

The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2 is a top view of one embodiment of a pelvic organ prolapse treatment device.

FIG. 3A is a top view of one embodiment of an assembly including a dilator insertable over a suture connected to an arm of the device illustrated in FIG. 2.

FIG. 3B is a top view and FIG. 3C is a perspective view of a knot employed to secure the suture to the arm of the device as illustrated in FIG. 3A.

FIG. 5 is a side view of a swelled/expanded dilator being assembled to an arm of the device illustrated in FIG. 2.

DETAILED DESCRIPTION

Figure 1A:
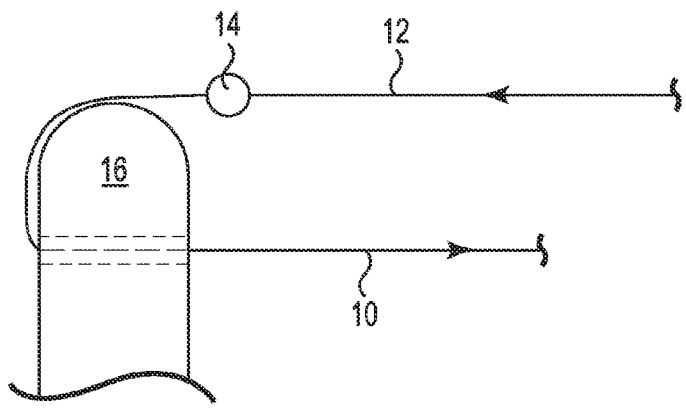
FIGS. 1A-1C illustrate a prior art suture line of an implant inserted into a ligament.
Figure 1B:
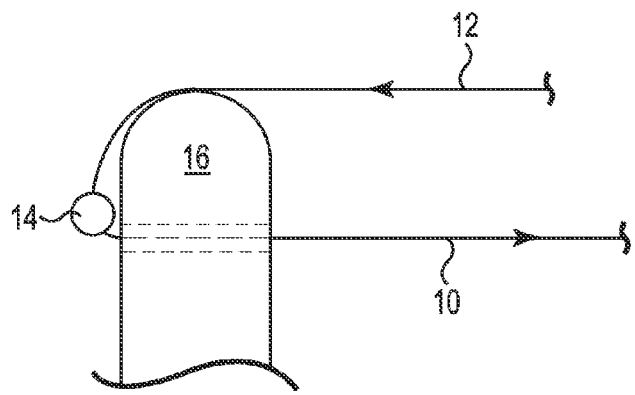
Figure 1C:
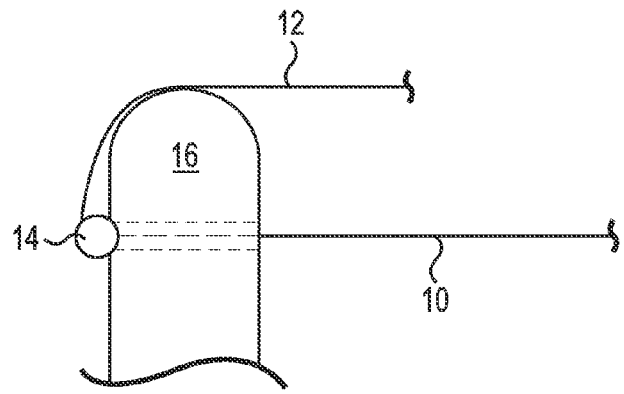

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

Embodiments provide an implant having a knot connecting a suture to an end portion of an arm, and a tubular dilator disposed over and permanently connected to the knot.

The phrase "permanently connected" means that the dilator does not separate from the knot/arm juncture without tearing the arm or otherwise damaging the implant. Removal of the dilator is achieved by cutting the arm of the implant and removing the severed portion of the arm and the dilator that is attached to the severed portion of the arm.

Embodiments provide an implant having a tubular dilator provided with an aspect ratio of greater than 7. The aspect ratio of the dilator is configured to allow the suture/arm juncture to be smoothly pulled through tissue when implanting the implant.

"Tubular dilator" means that a lateral cross-section of the dilator is circular. The dilator is provided with an annular wall surrounding an open channel (i.e., a tube), and a lateral cross-section of the tube of the dilator is circular.

"Aspect ratio" is defined to be the length of the dilator divided by the outside diameter of the dilator, represented as L/D. As an example, an aspect ratio of greater than 7 requires that the length of the dilator is at least a factor of 7 greater than the outside diameter of the dilator.

Embodiments provide an implantable support configured to treat urethrocele prolapse (the prolapse of the urethra into the vagina), a cystocele prolapse (the prolapse of the bladder into the vagina), a vault prolapse (the prolapse of the apex of the vagina, often after a hysterectomy), a uterine prolapse (the prolapse of the uterus into the vagina), an enterocele prolapse (the prolapse of the small bowel into the vagina), or a rectocele prolapse (the prolapse of the large intestine into the vagina). The implantable support includes an arm and a dilator that is placed over a portion of the arm, where the dilator facilitates movement of the arm through a tissue landmark.

FIG. 2 is a top view of one embodiment of an implantable support 50. The implantable support 50 includes a body portion 52, arms 54, 56, a suture 58 connected with the arm 54, and a dilator 60 disposed over a portion of the arm 54 and a portion of the suture 58.

The body portion 52 includes an edge 61 that extends between a first lateral side 62 and a second lateral side 64. In one embodiment, the implantable support 50 is formed to have a bilateral symmetry such that the first arm 54 is similar to the second arm 56. The body portion 52 is provided to support a prolapsed organ. In one embodiment, the body portion 52 is provided as a knitted polypropylene mesh, a woven polypropylene mesh, a knitted fabric, a woven fabric, a porous support formed of human tissue such as an allograft of pericardium, or a porous support formed of non-human or xenograft tissue. One suitable example of the implantable support 50 includes the body portion 52 fabricated of a knitted polypropylene mesh available from Coloplast Corp., Minneapolis Minn.

The arm 54 has a first end 70 connected to both the edge 61 and the first lateral side 62 of the body portion 52. In one embodiment, the arm 54 is attached by sewing, welding, or other means to the body portion 52. In one embodiment, the arm 54 is integrally woven or knitted as a monolithic piece of the body portion 52.

The suture 58 is attached to a second end 72 of the arm 54, for example with a knot as described below.

In one embodiment, the implantable support 50 is shaped and configured to treat a cystocele prolapse, or a prolapse on an anterior side of the vagina, and includes a tab 74 separate from the arm 54 that is connected to the body portion 52 opposite of the edge 61.

When implanted, each arm 54, 56 is desirably attached to a tissue landmark within the patient, for example a ligament, at a location that allows the body portion 52 to support the prolapsed organ. The dilator 60 is configured to be flexible to allow the dilator 60 to bend and flex as the arm 54 is drawn into and through the ligament. In addition, the dilator 60 is provided with a tapered profile that allows the arm 54 to be drawn through the tissue landmark with a reduced level of resistance.

FIG. 3A and FIG. 3B are top views of the suture 58 connected to the arm 54 of the support 50. In one embodiment, the suture 58 is attached to the second end 72 of the arm 54 by a knot 80. With reference to FIG. 3B, the second end 72 of the arm 54 is folded to include a first fold 82 and a second fold 84 that combine to reduce the lateral dimension of the second end 72 of the arm 54. The knot 80 is secured around the folded portions of the second end 72 of the arm 54 to capture both the arm 54 and the suture 58. In one embodiment, the knot 80 is located at a juncture of the arm 54 and the suture 58 (located where arrow 80 is pointing). In one embodiment, an excess portion 86 of the arm 54 is trimmed prior to attachment of the dilator 60.

FIG. 3C illustrates a perspective view of the knot 80. In one embodiment, the knot 80 is provided as a nail knot including opposing first and second ends 90, 92 that extend away from a winding 94 of the knot 80. With reference to FIGS. 3A and 3B, the suture 58 is inserted into the winding 94 prior to tightening of the knot 80 around the suture 58 and the second end 72 of the arm 54. In this manner, suture 58 is permanently attached to the arm 54. Alternatively, the knot 80 is formed by a portion of the suture 58 affixed to the second end 72 of the arm 54.

Figure 4A:
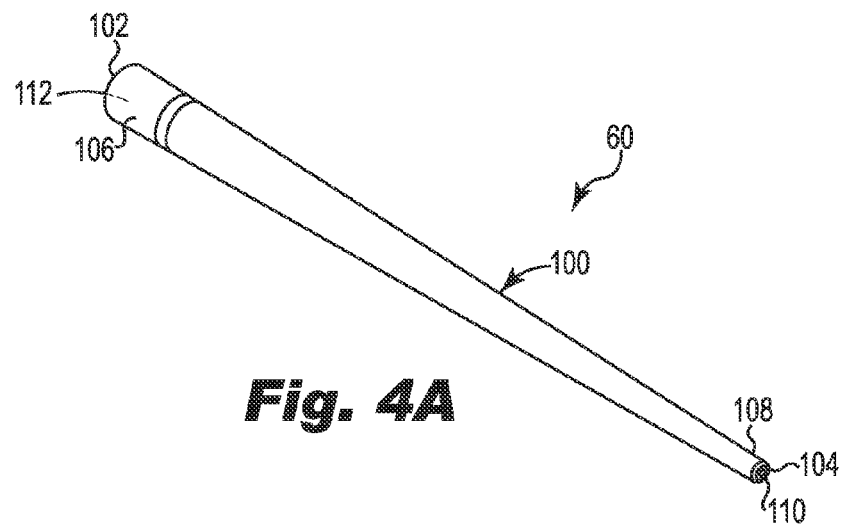
FIG. 4A is a perspective view.
Figure 4B:
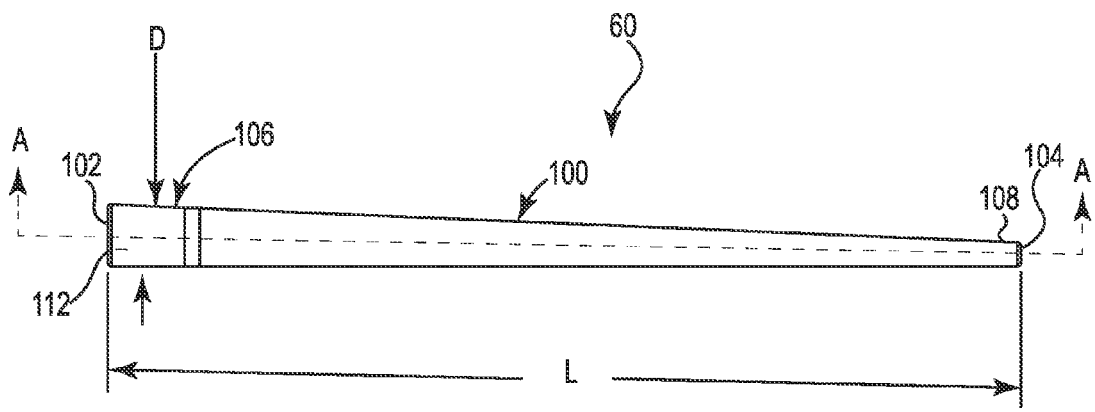
FIG. 4B is a side view.
Figure 4C:
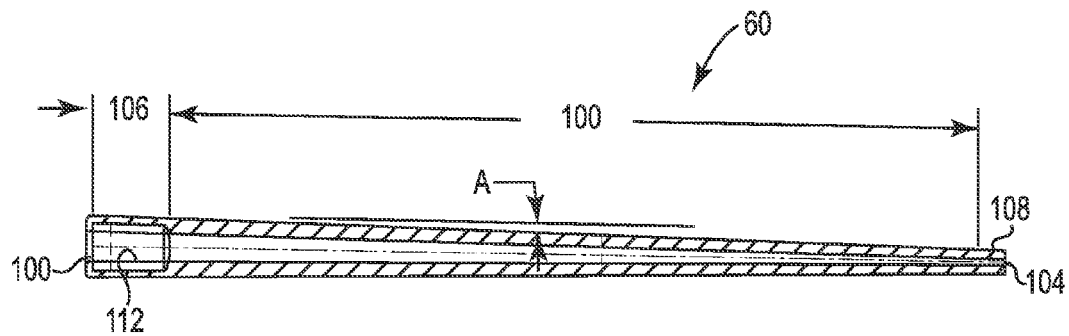
FIG. 4C is a cross-sectional view of one embodiment of a dilator of the device illustrated in FIG. 2.

FIG. 4A is a perspective view, FIG. 4B is a side view, and FIG. 4C is a cross-sectional view of one embodiment of a tubular, tapered dilator 60. The dilator 60 includes a central portion 100, a distal end 102, and a proximal end 104. The central portion 100 extends between a distal portion 106 and a proximal portion 108.

In one embodiment, the dilator 60 is a tubular dilator having an opening 110 sized to receive the suture 58 (FIG. 2), where the opening 110 extends to a recess 112 formed in the distal portion 106. The recess 112 is sized and configured to be secured over the knot 80 (FIG. 3C).

The dilator 60 generally tapers in a converging orientation from the distal portion 106 to the proximal portion 108. In one embodiment, the dilator 60 generally includes a tapered portion that has an angle A of taper in the range between 1-5 degrees. One suitable taper for the dilator has an angle A of taper of approximately 1.3 degrees.

In one embodiment, the dilator 60 has an overall length L extending between the distal end 102 and the proximal end 104 in the range between 1-2 inches, and preferably in the range between 1.25-1.75 inches. One suitable overall length L for the dilator 60 is approximately 1.38 inches.

In one embodiment, the dilator is provided with a diameter D measured at the distal portion 106 in the range between 0.080-0.125 inches, and preferably in the range between 0.090-0.1 inches. One suitable diameter D for the dilator 60 is approximately 0.094 inches.

The dilator 60 is configured to have an aspect ratio (i.e., L/D) in a range from 7-20. The dilator 60 is configured to have an aspect ratio of greater than 7, preferably the dilator 60 has an aspect ratio that is greater than 10, and more preferably the dilator 60 has an aspect ratio that is greater than 14. One suitable aspect ratio the dilator 60 is approximately 15 for an overall length L of 1.38 inches and a diameter D of 0.094 inches.

In one embodiment, the dilator 60 is fabricated from a plastic material that has a flexibility that is sufficient to allow the proximal end 104 to be bent through at least 180 degrees and into contact with the distal end 102. An example of one suitable plastic material is a solvent-swellable polyurethane having a durometer of between approximately 50-85 Shore D that provides the dilator 60 with a flexibility that is characterized by allowing the dilator 60 to be bent back upon itself. The dilator 60, when provided with this level of flexibility, is flexible or bendable enough to be formed into a circular arc associated with a circle having a radius between about 0.5-3 mm. A dilator with the flexibility to allow the dilator to bend through a circular arc associated with a radius of about 1 mm is suitably flexible to allow the dilator 60 to bend as it passes through a ligament.

In one embodiment, the dilator 60 is fabricated from a solvent-swellable polymer. One example of the dilator 60 is formed of a polymer that swells in the presence of toluene such that when the toluene evaporates the remaining shrunken polymer is permanently attached over the knot 80 and to the arm 54. In one embodiment, the dilator 60 is fabricated from a solvent-swellable polyurethane having a durometer of between approximately 50-85 Shore D.

One acceptable process for forming the dilator 60 includes dipping a mandrel of a desired shape repeatedly into a dispersion of polyurethane particles in a solvent carrier, and drying the dipped dilator between dips to remove solvent and leave a layer of polyurethane on the mandrel. The dilator 60, after multiple dipping and drying cycles, is thus formed over the mandrel. Thereafter, the formed polyurethane dilator 60 is introduced to a solvent, such as toluene, which swells the dilator 60 and allows it to be removed from the mandrel. The swelled polyurethane dilator 60 is placed over the knot 80 and the suture 58 and the solvent is evaporated off, resulting in the dilator 60 shrinking and becoming permanently attached to the knot 80.

FIG. 5 is a side view of a swelled dilator 60 being assembled to the arm 54 of the implant 50. In one embodiment, the dilator 60 is fabricated from polyurethane that is selected to swell in the presence of toluene. The dilator 60 swells when soaked in toluene to provide a larger dimension of the recess 112 that is sized to encompass the knot 80. In one embodiment, the recess 112 thus acquires a dimension that allows the distal portion 106 of the dilator 60 to be placed over the knot 80 and a portion of the arm 54 and a portion of the suture 58. As described above, the second end 72 of the arm 54 is folded to include the folds 82, 84 that constrict the arm 54 at the location where the knot 80 is placed. The toluene-swelled dilator 60 is placed over the knot 80 and over the second end 72 of the arm. Evaporation of the solvent shrinks the dilator 60 to permanently attach the dilator 60 to the arm 54 and the knot 80.

Figure 6:
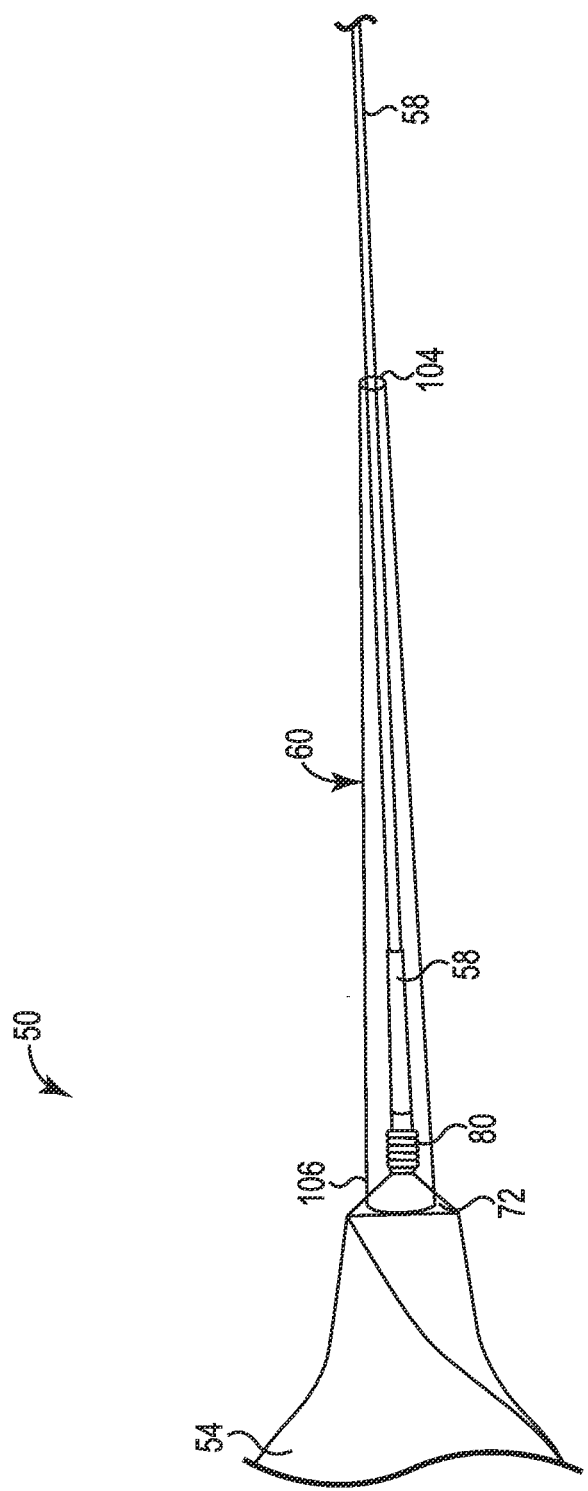
FIG. 6 is a side view of a dilator connected to a knot and a portion of an arm of the device illustrated in FIG. 2.

FIG. 6 is a side view of the dilator 60 permanently attached over the knot 80. In one embodiment, the distal portion 106 is secured over the knot 80 and a portion of the arm 54 and a portion of the suture 58. For example, the distal portion 106 is secured over the knot 80 and about a distance of 0.125 inches over a portion of the arm 54. The dilator 60 allows the arm 54 to follow the path of a needle with reduced resistance when placing the arm 54 into a tissue landmark.

In one embodiment, the recess 112 is swelled/expanded to a size that is just large enough to accommodate the knot 80, and evaporation of the solvent out of the dilator 60 shrinks the dilator 60 into a permanent attachment with the knot 80 only.

FIGS. 7A-7E are side views of one embodiment of the implantable support 50 introduced through tissue T.

Figure 7A:
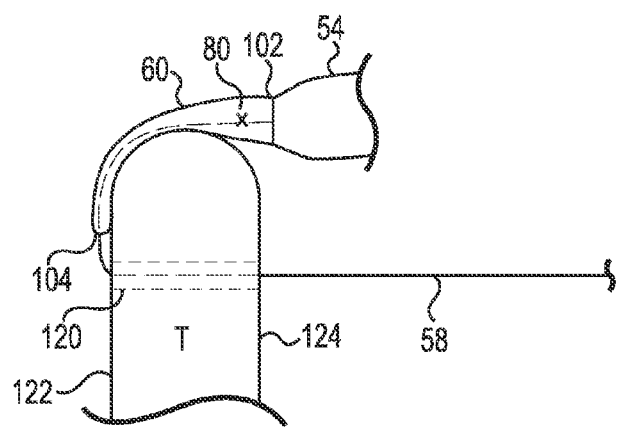
FIGS. 7A-7E are views of embodiments of an implantable support introduced through and engaged with tissue.

FIG. 7A is a schematic side view of the suture 58 pulling the arm 54 of the implantable support through a tissue landmark T. Examples of tissue landmarks T include muscles, tendons, and ligaments. The surgeon accesses the tissue landmark T through an incision, which is usually a vaginal incision that provides access to the sacrospinous ligament during a procedure to treat pelvic organ prolapse.

In one embodiment, the surgeon will first pass a needle through the tissue landmark T to form an opening 120. In one useful approach, the surgeon forms the opening 120 extending from a posterior side 122 to an anterior side 124 of the tissue landmark T, where the anterior side 124 is located nearest to the vaginal incision that provides the surgeon with access to the pelvic region. The suture 58 extends through the opening 120 and is employed to pull the arm 54 over a top portion of the tissue landmark T and through the opening 120.

Figure 7B:
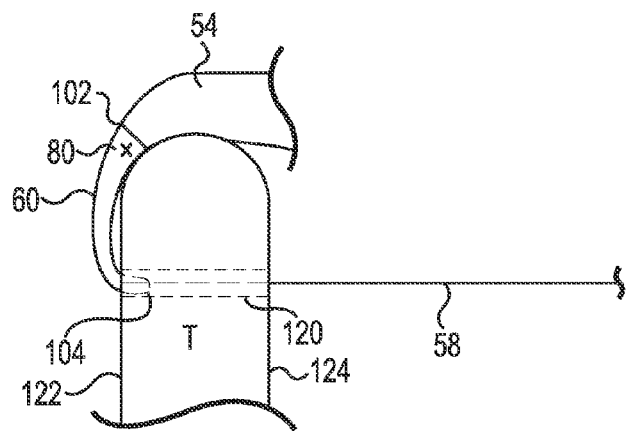

FIG. 7B is a schematic side view of the dilator 60 entering the opening 120 and moving from the posterior side 122 toward the anterior side 124 of the tissue landmark T. The dilator 60 is permanently secured to one or both of the arm 54 and/or the knot 80 and is suitably flexible to allow the proximal end 104 to bend as the dilator 60 and the arm 54 are pulled through the opening 120.

Figure 7C:
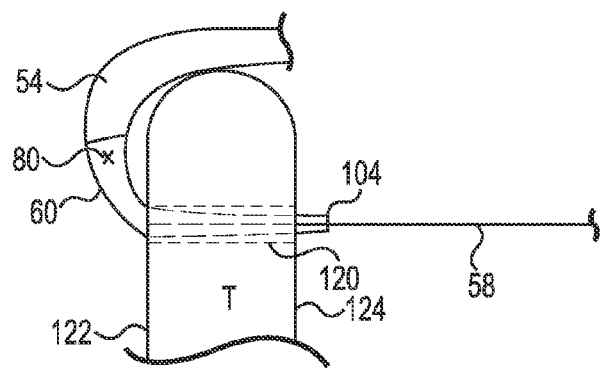

FIG. 7C is a schematic side view of the proximal end 104 of the dilator 60 passed through the tissue landmark T from the posterior side 122 to the anterior side 124. The dilator 60 has a suitably low coefficient of friction relative to the tissue to allow the dilator 60 to slide through the tissue landmark T. The tapered dilator 60 provides for a gradual transfer of the knot 80 through the opening 120 and through the tissue landmark T.

Figure 7D:
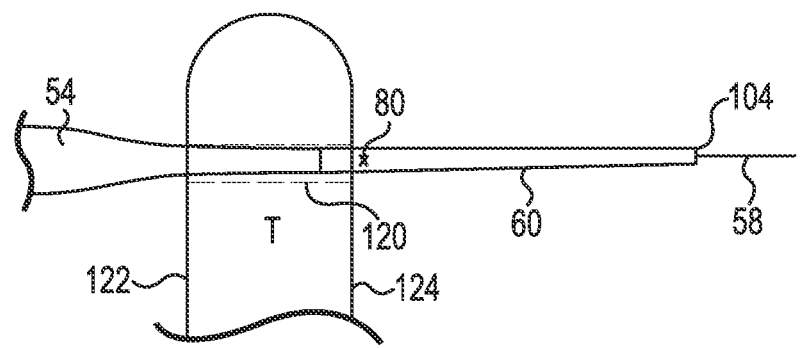

FIG. 7D is a schematic side view of the dilator 60 employed to smoothly transition the knot 80 from the posterior side 122 to the anterior side 124 of the tissue landmark T. In contrast to the devices that have an exposed knot or an exposed abrupt end of an implant, the dilator 60 allows the knot 80 that is attached to the suture 58 and the arm 54 to move smoothly through the tissue landmark T.

Figure 7E:
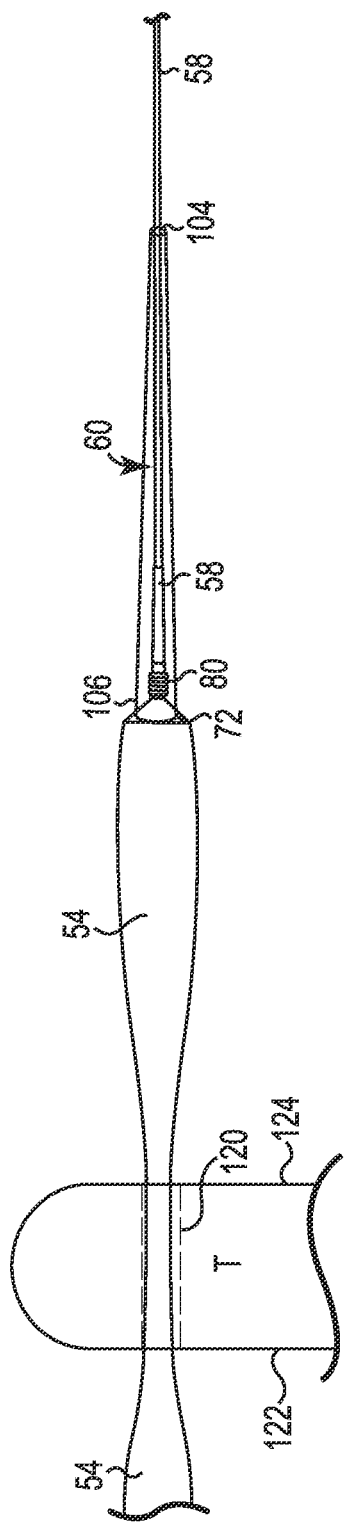

FIG. 7E is a schematic side view of the dilator 60 and a portion of the arm 54 after passage through the tissue T. The arm 54 is thus placed in the tissue T to anchor the body portion 52 of the implant 50 (FIG. 2) in a location selected to support and correct a prolapse of an organ. After such placement of the anchoring arm 54, the surgeon will trim off the excess portion of the arm 54 projecting past the anterior side 124 of the tissue T to remove the excess material of the arm 54 and the dilator 60.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A pelvic organ prolapse treatment device comprising:
an implantable support sized to support and treat a prolapsed organ of a patient, the implantable support including an arm having a first portion connected to a body of the implantable support and an end portion extending away from the body of the implantable support, with the end portion of the arm folded to include a first fold and a second fold that combine to reduce a lateral dimension of a portion of the end portion of the arm;
a suture extending away from the end portion of the arm;
a knot provided separately from the suture, the knot secured around the first fold and the second fold to capture both the end portion of the arm and the suture; and
a dilator disposed over and connected to the knot.

2. The device of claim 1, wherein the dilator is permanently connected to the knot.

3. The device of claim 1, wherein the dilator is permanently connected to the arm.

4. The device of claim 1, wherein the dilator surrounds a circumference of the knot.

5. The device of claim 1, wherein the dilator has an aspect ratio of greater than 7.

6. The device of claim 5, wherein the aspect ratio of the dilator is provided in a range from 7-20.

7. The device of claim 6, wherein the aspect ratio of the dilator is provided in a range from 10-15.

8. The device of claim 1, wherein the dilator has a durometer of between 50-85 Shore D.

9. The device of claim 1, wherein the dilator is a tubular dilator.

10. The device of claim 1, wherein the dilator is a tapered dilator that tapers in a converging orientation from a distal end connected to the knot to a proximal end.

11. The device of claim 10, wherein the tapered dilator has a flexibility characterized in that the tapered dilator bends through at least 180 degrees such that the proximal end is displaceable to contact the distal end.

12. The device of claim 10, wherein the tapered dilator has a flexibility characterized in that the tapered dilator bends through an arc associated with a circle having a radius of about 1 mm.

13. The device of claim 10, wherein the tapered dilator has an angle of taper in a range between 1-5 degrees.

14. The device of claim 1, wherein the dilator is fabricated from a solvent-swellable plastic.

15. The device of claim 1, wherein the dilator is disposed over a portion of the suture.

* * * * *